(12) United States Patent
Baars et al.

(10) Patent No.: US 6,525,229 B2
(45) Date of Patent: Feb. 25, 2003

(54) PROCESS FOR SEPARATING ETHYLENE GLYCOL

(75) Inventors: Hendrikus Jacob Baars, Amsterdam (NL); Alouisius Nicolaas Rene Bos, Amsterdam (NL); Jelte Kars, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/871,281

(22) Filed: May 31, 2001

(65) Prior Publication Data

US 2002/0029954 A1 Mar. 14, 2002

(30) Foreign Application Priority Data

May 31, 2000 (EP) .............................. 00304580

(51) Int. Cl.[7] ......................... C07C 27/26; C07C 29/74; C07C 31/18
(52) U.S. Cl. ........................................ 568/872; 568/868
(58) Field of Search ................................. 568/872, 868

(56) References Cited

U.S. PATENT DOCUMENTS 3,904,656 A * 9/1975 Broz ................... 260/348.5 R
4,822,926 A * 4/1989 Dye ............................ 568/867
6,184,423 B1   2/2001 Jen ............................ 568/854

FOREIGN PATENT DOCUMENTS

GB    2091580 A      8/1982   ........... B01D/15/08
GB    2 091 580 A  * 8/1982

* cited by examiner

*Primary Examiner*—Johann Righter
*Assistant Examiner*—Elvis O. Price

(57) ABSTRACT

A process for separating ethylene glycol from its aqueous mixture with organic acids, salts and unidentified UV light absorbers, the process comprising the steps of a) flashing the aqueous mixture under conditions effective to produce a bottom slurry containing the salts and an overhead aqueous fraction containing the ethylene glycol, the acids and the unidentified UV light absorbers;

b) passing the overhead aqueous fraction from step a) through at least one bed of ion exchange resin effective to produce a product stream having a reduced UV light absorbance; and c) drying the product stream of step b) in a dehydrator.

13 Claims, No Drawings

PROCESS FOR SEPARATING ETHYLENE GLYCOL

The present invention relates to a process for separating ethylene glycol from its aqueous mixture with organic acids and salts. Such mixtures are generated in particular in the industrial production of ethylene oxide.

BACKGROUND OF THE INVENTION

Ethylene oxide is an important base chemical. It can be used as such and as an intermediate for various chemicals. Most ethylene oxide, however, is hydrolysed to produce ethylene glycol.

Herein unless otherwise specified the term "ethylene glycol" is used in a generic sense to denote all ethylene glycols produced from the reaction of ethylene oxide with water, and therefore encompasses for example monoethylene glycol, diethylene glycol, triethylene glycol, tetraethylene glycol, etc.

Ethylene oxide is produced by catalytic gas-phase oxidation of ethylene with oxygen. The hot reaction gas containing ethylene oxide is cooled rapidly and supplied to an absorption column wherein water is added to dissolve the ethylene oxide. The fat absorbent is then stripped with steam in a stripping column to release the ethylene oxide, the remaining lean absorbent being re-circulated to the absorption column. In many cases the absorption column proper is preceded by a separate quench section wherein the entering reaction gas is scrubbed by a cooled recirculated slightly alkaline aqueous quench stream to absorb and neutralise organic acids (such as formic acid, acetic acid and oxalic acid) which are typical by-products of the ethylene oxidation reaction. This neutralisation is maintained by the continuous addition of a caustic solution (typically sodium hydroxide) to the aqueous quench stream. Apart from the organic acids, carbon dioxide which is also present in the reaction gas also reacts with the added caustic and forms carbonate and bicarbonate. In aqueous solution these salts are completely dissociated and the organic acids are partly dissociated. When an organic acid is removed from the mixture, such as happens during flashing or distillation, it will be formed again from the respective salt in the bottom fraction, resulting in a rise of pH which will eventually reduce the formation of acid.

In order to maintain the water balance and prevent by-products from accumulating in the system, some fresh water is continuously added and the absorption column as well as the stripping column are purged. The purge stream from the (quench section of) the absorption column is herein termed the "quench bleed stream" and the purge stream from the stripping column is herein termed the "stripper bleed stream". Both contain important amounts of valuable components.

The quench bleed stream originally contains, beside the above-mentioned by-products (salts and acids) and water, mainly ethylene oxide as its valuable component. In order to recover this ethylene oxide, the quench bleed stream can be stripped in a quench bleed stripper whereby the bottom solution which contains the by-products is discarded. Alternatively, as is disclosed in U.S. Pat. No. 4,822,926, the quench bleed stream is subjected to elevated temperature and pressure conditions in order to hydrolyse the ethylene oxide present therein to ethylene glycol. In that case the ethylene glycol is the valuable component of the hydrolysed quench bleed stream, which has to be separated from the by-products and dried.

The stripper bleed stream contains, beside the above-mentioned by-products (salts and acids) and water, mainly ethylene glycol which has been formed from ethylene oxide and water under the elevated temperature and pressure conditions of the stripping column. Again, the ethylene glycol is the valuable product of the stripper bleed stream, which has to be separated from the by-products and dried.

Usually, the ethylene glycol present in the quench bleed stream and in the stripper bleed stream is flashed and, if necessary, further dried in a dehydrator, which is essentially a distillation column wherein the water is evaporated. However, the dried product then still contains organic acids.

The organic acids are detrimental to the quality of the ethylene glycol, in that they are ultra-violet (UV) light absorbers. By reacting with the glycols, especially in the absence of water, the acids may form esters which are also UV light absorbers. Other, unidentified, UV light absorbers may also be present in the ethylene glycol containing streams.

It is an aim of the present invention to produce from the hydrolysed quench bleed stream and the stripper bleed stream an ethylene glycol stream from which monoethylene glycol of high (fibre grade) quality, which is essentially free of salts and organic acids and which has a high UV light transmittance (i.e. low UV light absorbance), can be obtained.

According to U.S. Pat. No. 4,822,926 the salts from the quench bleed stream are separated off by centrifuging the bottom slurry produced by the dehydrator, followed by passing the centrifuged liquid phase to a glycol flasher. However, there is no mention in this document of the acids, nor of their effect on UV light absorbance.

According to U.S. Pat. No. 3,904,656 the stripper bleed stream is upgraded by treatment with ion exchange materials to remove metal salts, by degassing to remove carbon dioxides and volatiles, and by treatment with activated carbon to remove UV light absorbers. A drawback of this method is that the ion exchange material when used to remove the salts will be exhausted very quickly. A second and similar drawback is that the capacity of an active carbon bed for removing UV light absorbers has been found to be disappointingly low.

GB-A 2 091 580 discloses a method for recovering ethylene glycol from washings containing ethylene glycol, organic acids and coloured materials, which comprises subjecting the washings to chromatography wherein a salt form of a cation exchange resin is used as the packing material, and water is used as the eluent. This document ignores the presence of salts in the washings.

SUMMARY OF THE INVENTION

A process for separating ethylene glycol from its aqueous mixture with organic acids, salts and UV light absorbers, the process comprising the steps of a) flashing the aqueous mixture under conditions effective to produce a bottom slurry containing the salts and an overhead aqueous fraction containing the ethylene glycol, the acids and the UV light absorbers;

b) passing the overhead aqueous fraction from step a) through at least one bed of ion exchange resin effective to produce a product stream having a reduced UV light absorbance; and c) drying the product stream of step b) in a dehydrator.

DETAILED DESCRIPTION OF THE INVENTION

The present invention relates to a process for separating ethylene glycol from its aqueous mixture with organic acids, salts and unidentified UV light absorbers, the process comprising the steps of a) flashing the aqueous mixture under conditions effective to produce a bottom slurry containing the salts and an overhead aqueous fraction containing the ethylene glycol, the acids and the unidentified UV light absorbers;

b) passing the overhead aqueous fraction from step a) through at least one bed of ion exchange resin effective to produce a product stream having a reduced UV light absorbance; and c) drying the product stream of step b) in a dehydrator. Typically, the aqueous mixture is the hydrolysed quench bleed stream and/or the stripper bleed stream of an ethylene oxide production plant.

In step b), preferably the ion exchange resin is an anion exchange resin. More preferably a combination of an anion exchange resin with a cation exchange resin is used. Such combination may be done in a mixed bed of anion and cation exchange resins or in two subsequent beds. Most preferably a bed of anion exchange resin is used, followed by a bed of cation exchange resin.

An important feature of the present invention is that in the sequence of steps a) and b) the salts are removed firstly and the organic acids and optionally other UV light absorbers are removed secondly, thereby avoiding rapid exhaustion of the ion exchange resin used in step b) with salts. The removal of the organic acids is important for producing high quality (fibre grade) mono-ethylene glycol, since the organic acids are UV light absorbers. The removal of the organic acids before the drying of the product stream in step c) is important because, as noted above, in the absence of water organic acids tend to react with glycols to form esters which are also UV light absorbers. Once formed, the esters cannot be removed with an ion exchange resin and, depending on their boiling point, they will tend to remain in the glycol.

In step a) of the process according to the present invention the flashing conditions which are effective to produce a bottom fraction and an overhead fraction as defined above are generally a temperature in the range of from about 50 to about 200° C., and a pressure in the range of from about 0.1 to about 100 kPa. Preferably they are from about 120 to about 180° C. and from about 5 to about 30 kPa, for example from about 120 to about 140° C. and from about 5 to about 15 kPa.

Step a) of the present process may be performed in batch operation or in continuous flow operation. In the latter case the Volume Hourly Space Velocity (VHSV) is generally a VHSV in the range of from about 1 to about 25 v/v, based on the volume of the flashing column.

In step b) of the process according to the present invention the ion exchange material may be chosen from any one of the ion exchange materials known in the art. Particularly suitable are the strongly basic anion exchange resins (IER's) wherein the basic groups are quaternary ammonium or quaternary phosphonium, although basic ion exchange resins wherein the basic groups are tertiary amine or tertiary phosphine may also be used.

Strongly basic anionic exchange resins which are suitable for use in step b) of the present process are known per se and many are commercially available, e.g. the ones sold under the trade names AMBERJET 4400, AMBERLITE 400, AMBERLITE IRA 404, LEWATIT M 500 KR, LEWATIT OC 1243, DOWEX 1×8, DOWEX MSA-1 (all of which are products based on polystyrene, cross-linked with divinylbenzene) and REILLEX HPQ (which is based on polyvinyl-pyridine, cross-linked with divinylbenzene) (AMBERJET, AMBERLITE, LEWATIT, DOWEX and REILLEX are trademarks).

Basic anionic exchange resins which are suitable for use in step b) of the present process are known per se and many are commercially available, e.g. the ones sold under the trade names DUOLITE A 368, DUOLITE A 365, AMBERLITE IRA 67, AMBERLITE IRA 96 and IMAC HP 661 (DUOLITE and IMAC are trademarks).

Anion exchange resins in the $OH^-$ form are the most efficient for the removal of acids through the formation of water with the proton of the acid. In that case the pH of the product stream becomes close to neutral. Anion exchange resins in their salt form, such as the $Cl^-$, $NO_3^-$ or $SO_4^=$ form, may also be used—but then the equivalent strong acids, such as HCl, $HNO_3$ and $H_2SO_4$ will be formed and the product stream will become more acidic and will have to be neutralised. This can suitably be done by adding alkaline compounds such as alkali metal hydroxides, especially NaOH or KOH, or alkaline earth metal hydroxides. The resulting salts will remain in the bottom streams of all subsequently performed distillation steps without affecting the quality of the purified glycol. Alternatively, cation exchange resins containing alkali metal ions such as e.g. $Na^+$ or $K^+$, or alkaline earth metal ions may be used to neutralise acidic product stream.

Even when an anion exchange resin in its $OH^-$ form is used and the pH of the product stream is neutral, it is preferred to add a cation exchange resin in order to capture any degradation products, such as amines, which may be released from the anion exchange resin during operation. Moreover it has quite surprisingly been found that a cation exchange bed, even when used alone in step b), will also produce a product stream having a reduced UV light absorbance. As this cannot be due to a removal of organic acids from the product stream, it must be due to the removal of other and presently unidentified UV light absorbents.

When the anion exchange resin is in its $OH^-$ form the cation exchange resin can best be in its $H^+$ form, while when the anion exchange resin is in its salt form, resulting as explained above in an acidic product stream which has to be neutralised, the cation exchange resin must also be in its salt form.

When a combination of anion and cation exchange resin is used, it can suitably be applied in the form of a mixed bed, but more preferably it is applied as two separate beds with the cation exchange resin being the second bed. This has the advantage that the ion exchange resin beds can be regenerated more easily, when eventually necessary, by conventional methods such as using an alkali, e.g. NaOH, or a strong mineral acid, e.g. HCl or $H_2SO_4$.

There are three types of acidic ion exchange resins in commercial use, i.e. the strongly acidic ion exchange resins of the sulphonic type, the acidic ion exchange resins of the acrylate type and the weakly acidic ion exchange resins of the methacrylate type. A strongly acidic ion exchange resin, i.e. one of the sulphonic type, is best suited. However, it will be understood that one or both of the two other types, either alone or in combination with the sulphonic type, is also within the scope of the present invention.

Examples of commercially available weakly acidic ion exchange resins of the methacrylate type are those known by the trade marks AMBERLITE IRC-50, AMBERLITE GC-50, AMBERLITE IRP-64 and AMBERLITE IRP-88.

Examples of commercially available acidic ion exchange resins of the acrylate type are those known by the trade marks AMBERLITE IRC-86, AMBERLITE IRC-76, IMAC HP 336 and LEWATIT CNP 80.

Examples of commercially available strongly acidic ion exchange resins of the sulphonic type are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT OC 1213, LEWATIT S 100 MB and LEWATIT S 100 G1 (AMBERLYST and DIANON are trademarks).

In terms of exchange capacity or equivalent of active sites, the relative amount of acidic ion exchange resin to be used according to the present invention is generally in the range of from 50 to 200%, based on the total capacity of the strongly basic ion exchange resin. Preferably this amount is in the range of from 75 to 150%, more preferably from 90 to 110%.

Step (b) is suitably carried out at a temperature not higher than 40° C., which can be any temperature in the range of from about 0 to about 40° C., provided that the overhead fraction remains substantially in the liquid phase.

In step b) of the present process the overhead fraction of step a) is passed through the bed of cationic exchange resin and/or anionic exchange resin in a Liquid Hourly Space Velocity (LHSV) in the range of from, for example, about 0.1 to about 100, suitably about 1 to about 25 and conveniently about 1 to about 10, v/v, based on the amount of resin in the bed.

A most important advantage of steps a) and b) being performed in the given sequence is, that the capacity of the ion exchange bed is not used up for removing salts and it does not have to be regenerated frequently. Separate beds of anionic and cationic exchange resin can be regenerated by conventional methods, such as using a mineral acid, e.g. hydrochloric acid or sulphuric acid, or an alkali, e.g. sodium hydroxide, respectively.

In the final step c) of the process according to the present invention the product stream of step b), which now contains substantially pure ethylene glycol and water, is dried in a dehydrator (which is most suitably a flashing or distillation column). This can be a dedicated dehydrator, or alternatively the product stream of step b) can be added to the bulk of the ethylene glycol which is produced from the mainstream of the ethylene oxide in the plant and sent to a common dehydrator.

When the dehydrator is a flashing column, this is operated under conventional conditions suitable for removal of water from ethylene glycol.

Following dehydration it can be useful to separate out monoethylene glycol product from the heavier ethylene glycols. This separation is conveniently carried out by methods well known in the art, for example by distillation.

The following Examples will illustrate the invention. "Ambient" conditions are 20 to 25° C. and 100 kPa.

EXAMPLES

An aqueous sample of an ethylene oxide (EO) stripper bleed stream from a commercial plant was used in these Examples. The aqueous sample contained about 61 wt % of Mono-Ethylene Glycol (MEG), 4.9 wt % of Di-Ethylene Glycol (DEG), 0.2 wt % of Tri-Ethylene Glycol(TEG), 0.5 wt % or less of salts and no detectable EO.

Step a)

The bleed stream sample was subjected to flashing in a single-tray rotating film evaporator at 130° C. and a pressure declining from ambient to 0.1 kPa, whereby about 0.53 wt % of bottom slurry (containing the salts) was removed, the overhead fraction contained about 33.9 wt % of water, 61.4 wt % of MEG, 4.7 wt % of DEG and no detectable EO.

Step b)

The overhead fraction was divided into eight batches, of which the first served as a blank and was not passed through a resin bed (Comparative Example 1) and 1 liter of each of the other seven was passed, at a Liquid Hourly Space Velocity (liter feed per liter resin per hour) of 10, through one or two beds of ion exchange resin as follows:

Example 2—AMBERJET 4400 (OH⁻), 15 ml;
Example 3—LEWATIT M500 KR (OH⁻), 15 ml;
Example 4—AMBERLYST 15 (H⁺), 15 ml
Example 5—AMBERJET 1500 H (H⁺), 15 ml;
Example 6—AMBERJET 4400 (OH⁻) followed by AMBERLYST 15 (H⁺), 15 ml each;
Example 7—LEWATIT M500 KR (OH⁻) mixed with AMBERLYST 15 (H⁺), 15 ml (total); and
Example 8—LEWATIT M500 KR (OH⁻) followed by AMBERJET 1500 H, 15 ml each.

AMBERJET 4400 is a strongly basic anion exchange resin produced by Rohm & Haas. LEWATIT M 500 KR is a strongly basic anion exchange resin produced by Bayer. AMBERLYST 15 and AMBERJET 1500 H are strongly acidic cation exchange resins produced by Rohm & Haas.

Step c)

The eight batches (Examples 1–8) were subjected to the following treatment in order to isolate the MEG:

First each of the eight batches (Examples) was flashed in a single-tray rotating film evaporator at 130° C. and a pressure declining from ambient to 15 kPa in order to separate off as overhead the major part of the water contained therein. Secondly the flashing-bottom fraction of each batch was subjected to distillation at 130° C. and 1.5 kPa in a 30 trays full glass column, diameter 2.5 cm. The distillation-overhead produced by this distillation of each batch (Example) contained about 96 wt % of the amount of MEG originally present in the 1 liter used in step b) and was substantially free of water and DEG.

Results: Quality Testing of the MEG Batches (Examples) Produced in Step c)

Quality testing was performed by measuring the UV light transmittance of each of the eight fractions of each of the eight Examples against distilled water in an UVIKON 932 spectrophotometer, at wavelengths of 220, 275 and 350 nm (UVIKON is a trademark). The results are presented in the following Table I

TABLE I

| | | MEG % UV transmittance at wavelength | | |
|---|---|---|---|---|
| Example | Resin treatment | 220 nm | 275 nm | 350 nm |
| 1 (Comp) | None | 82.2 | 93.4 | 99.4 |
| 2 | AMBERJET 4400 (OH⁻) | 87.0 | 97.4 | 99.6 |
| 3 | LEWATIT M500 KR (OH⁻) | 90.3 | 98.4 | 100.1 |
| 4 | AMBERLYST 15 (H⁺) | 86.5 | 95.7 | 100.0 |
| 5 | AMBERJET 1500 H (H⁺) | 91.2 | 98.6 | 99.5 |
| 6 | AMBERJET 4400 followed by AMBERLYST 15 | 91.2 | 98.3 | 99.7 |
| 7 | LEWATIT M500 KR mixed with AMBERLYST 15 | 90.4 | 98.4 | 99.9 |
| 8 | LEWATIT M500 KR followed by AMBERJET 1500 H | 93.3 | 99.0 | 100.2 |

From these results the general conclusion may be drawn, that the UV transmittance of the product MEG was improved by all seven ion exchange treatments at all three wavelengths tested, especially at the shorter wavelengths where the quality of the untreated MEG was least good.

We claim:

1. A process for separating ethylene glycol from its aqueous mixture with organic acids, salts and UV light absorbers, the process comprising the steps of
   a) flashing the aqueous mixture under conditions effective to produce a bottom slurry containing the salts and an overhead aqueous fraction containing the ethylene glycol, the acids and the UV light absorbers;
   b) passing the overhead aqueous fraction from step a) through at least one bed of ion exchange resin effective to produce a product stream having a reduced UV light absorbance; and
   c) drying the product stream of step b) in a dehydrator.

2. The process of claim 1 wherein the aqueous mixture is the hydrolysed quench bleed stream and/or the stripper bleed stream of an ethylene oxide production plant.

3. The process of claim 1 wherein the ion exchange resin in step b) is an anion exchange resin.

4. The process of claim 1 wherein the ion exchange resin in step b) is a cation exchange resin.

5. The process of claim 1 wherein the ion exchange resin in step b) is a mixed bed of anion exchange resin and cation exchange resin.

6. The process of claim 1 wherein in step b) a bed of anion exchange resin followed by a bed of cation exchange resin is used.

7. The process of claim 6 wherein in step b) the anion exchange resin is in the $OH^-$ form and the cation exchange resin, is in the $H^+$ form.

8. The process of claim 5 wherein step b) the anion exchange resin is in the $OH^-$ form and the cation exchange resin, is in the $H^+$ form.

9. The process of claim 7 wherein the aqueous mixture is the hydrolyzed quench bleed stream and/or the stripper bleed stream of an ethylene oxide production plant.

10. The process of claim 8 wherein the aqueous mixture is the hydrolyzed quench bleed stream and/or the stripper bleed stream of an ethylene oxide production plant.

11. The process of claim 3 wherein the anion exchange resin is in the $OH^-$ form.

12. The process of claim 4 wherein the cation exchange resin is in the $H^+$ form.

13. The process of claim 1 wherein the flashing is carried out at a temperature in the range of from about 50 to about 200° C. and a pressure in the range of from about 0.1 to about 100 kPa.

* * * * *